United States Patent [19]
Heller et al.

[11] Patent Number: 5,955,520
[45] Date of Patent: Sep. 21, 1999

[54] PHOTOCHROMIC INDENO-FUSED NAPHTHOPYRANS

[75] Inventors: Harry G. Heller, Cardiff; Julian R. Levell, Lyne, both of United Kingdom

[73] Assignee: PPG Industries, Inc., Pittsburgh, Pa.

[21] Appl. No.: 08/666,726

[22] Filed: Jun. 17, 1996

[51] Int. Cl.$^6$ .............................. C08K 5/34; C08K 5/15; C08K 413/00

[52] U.S. Cl. .............................. 524/87; 524/99; 524/104; 524/110; 544/124; 544/148; 544/150; 546/167; 546/194; 546/196; 546/197; 546/280.7; 546/281.1; 546/284.1; 548/454; 548/518; 548/525; 548/526; 549/58; 549/60; 549/356; 549/362; 549/382

[58] Field of Search .............................. 549/58, 60, 356, 549/362, 382; 548/525, 526, 518, 454; 546/167, 194, 196, 197, 280.1, 281.1, 284.1; 544/124, 148, 150; 524/87, 99, 104, 110

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/300 |
| 4,563,458 | 1/1986 | Widdig et al. | 514/253 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/586 |
| 4,931,221 | 6/1990 | Heller et al. | 252/586 |
| 5,066,818 | 11/1991 | Van Gemert et al. | 549/389 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,369,158 | 11/1994 | Knowles | 524/110 |
| 5,384,077 | 1/1995 | Knowles | 252/586 |
| 5,395,567 | 3/1995 | Van Gemert et al. | 252/586 |
| 5,405,958 | 4/1995 | Van Gemert et al. | 544/71 |
| 5,429,774 | 7/1995 | Kumar | 252/586 |
| 5,451,344 | 9/1995 | Knowles et al. | 252/586 |
| 5,458,814 | 10/1995 | Kumar et al. | 252/586 |
| 5,466,398 | 11/1995 | Van Gemert et al. | 252/586 |
| 5,514,817 | 5/1996 | Knowles | 549/384 |
| 5,552,090 | 9/1996 | Knowles | 252/586 |
| 5,565,147 | 10/1996 | Knowles et al. | 252/586 |
| 5,578,252 | 11/1996 | Van Gemert et al. | 252/586 |
| 5,585,042 | 12/1996 | Van Gemert | 252/586 |
| 5,645,767 | 7/1997 | Van Gemert | 252/586 |

FOREIGN PATENT DOCUMENTS

| | | |
|---|---|---|
| 246114 | 11/1987 | European Pat. Off. . |
| 250193 | 12/1987 | European Pat. Off. . |
| 294056 | 12/1988 | European Pat. Off. . |
| 62-195383 | 6/1987 | Japan . |
| 02/69471 | 3/1990 | Japan . |

OTHER PUBLICATIONS

*Friedel–Crafts and Related Reactions*, George A. Olah, Interscience Publishers, vol. 3, Chap. XXXI, pp. 1–8, 1964.

"Regioselective Friedel Crafts Acylation of 1,2,3,4–Tetrahydroquinoline and Related Nitrogen Heterocycles: Effects of NH Protective Groups and Ring Size", Ishihara, Y., et al, J. Chem. Soc., Perkin Trans. 1, pp. 3401–3406, 1992.

"1–Phenylnaphthalenes. part IV. The Cyclisation of Methyl Hydrogen cis and trans–γ–o–Methoxyphenyl–and Ethyl Hydrogen cis—and trans–γ–p–Methoxyphenyl–γ–phenylitaconate to the Corresponding 1–Phenylnaphthalenes", Baddar, F.G. et al., Journal of the Chemical Society, pp. 986–994, 1958.

"Behavior of α–Substituted Chalcones on Attempted Friedel–Crafts Arylation", Koelsch, C.F., The Journal of Organic Chemistry, vol. 26, pp. 2590–2592, 1961.

*The Chemistry of the Carbonyl Group*, Saul Patai, Editor, Interscience Publishers, Chapter 11, pp. 507–566, 1966.

*Primary Examiner*—Kriellion S. Morgan
*Attorney, Agent, or Firm*—Irwin M. Stein; Frank P. Mallak

[57] ABSTRACT

Described are novel photochromic indeno-fused naphthopyran compounds, examples of which are naphthopyran compounds having a substituted or unsubstituted indeno group, the 2,1 positions of which are fused to the f side of the naphtho portion of the naphthopyran, and having certain substituents at the 3-position of the pyran ring. Certain substituents may also be present at the number 5, 6, 7, 8, 9, 10, 11, 12 or 13 carbon atoms of the compounds. These compounds may be represented by the following graphic formula:

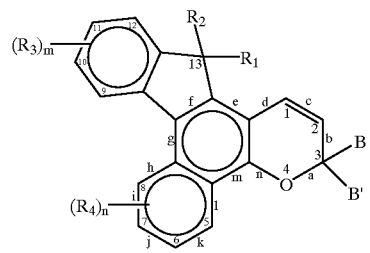

Also described are polymeric organic host materials that contain or that are coated with such compounds. Optically clear articles such as ophthalmic lenses or other plastic transparencies that incorporate the novel naphthopyran compounds or combinations thereof with complementary photochromic compounds, e.g., certain other naphthopyrans, benzopyrans and spiro(indoline)type compounds, are also described.

25 Claims, No Drawings

PHOTOCHROMIC INDENO-FUSED NAPHTHOPYRANS

DESCRIPTION OF THE INVENTION

The present invention relates to certain novel naphthopyran compounds. More particularly, this invention relates to novel photochromic indeno-fused naphthopyran compounds and to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b] pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho-[1,2-b]pyrans without the aforementioned additives ranges from several hours to many days to reach complete reversion. U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions.

The present invention relates to novel substituted naphthopyran compounds having a substituted or unsubstituted indeno group, the 2,1 positions of which are fused to the f side of the naphtho portion of a 2H-naphtho[1,2b]pyran, and having certain substituents at the 3-position of the pyran ring. These compounds have unexpectedly been found to demonstrate a bathochromic shift for the wavelength in the visible spectrum at which the maximum absorption of the activated (colored) form of the photochromic compound, i.e., the lambda max (Vis), occurs, thereby resulting in activated colors ranging from orange to blue/gray. In addition, these compounds have demonstrated a high molar absorptivity (or molar extinction coefficient) in the UV, an acceptable fade rate without the addition of acids or bases, a high activated intensity, and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 1H-indeno[2,1-f]naphtho[1,2-b]pyrans having activated colors ranging from orange to blue/gray, an acceptable fade rate, high activated intensity and a high coloration rate may be prepared. These compounds may be described as indeno fused [1,2-b] naphthopyrans having certain substituents at the 3 position of the pyran ring. Certain substituents may also be present at the number 5, 6, 7, 8, 9, 10, 11, 12, or 13 carbon atoms of the compounds. These compounds may be represented by the following graphic formula I in which the letters a through n represent the sides of the naphthopyran ring, and the numbers identify the ring atoms of the indeno-fused naphthopyran. In the definitions of the substituents shown in formula I, like symbols have the same meaning unless stated otherwise.

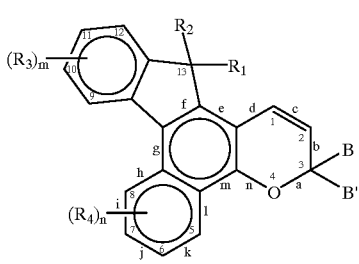

In graphic formula I, $R_1$ may be hydrogen, hydroxy or chloro and $R_2$ may be the group, —CH(V)$_2$, wherein V is —CN or —COOR$_5$, and each $R_5$ is hydrogen, $C_1$–$C_6$ alkyl, phenyl($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, or the unsubstituted, mono- or di-substituted aryl groups phenyl or naphthyl, or $R_2$ may be the group, —CH($R_6$)Y, wherein $R_6$ is hydrogen, $C_1$–$C_6$ alkyl or the unsubstituted, mono- or di-substituted aryl groups phenyl or naphthyl, and Y is —COOR$_5$, —COR$_7$, or —CH$_2$OR$_8$, wherein $R_7$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, e.g. dimethyl amino, methyl propyl amino, etc., phenylamino, mono- or di-($C_1$–$C_6$)alkyl substituted phenylamino, mono- or di-($C_1$–$C_6$)alkoxy substituted phenylamino, diphenylamino, mono- or di($C_1$–$C_6$)alkyl substituted diphenylamino, i.e., each phenyl has one or two $C_1$–$C_6$ alkyl substituents, mono- or di-($C_1$–$C_6$)alkoxy substituted diphenylamino, morpholino, or piperidino; $R_8$ is hydrogen, —COR$_5$, $C_1$–$C_6$ alkyl, $C_1$–$C_3$ alkoxy($C_1$–$C_6$)alkyl, phenyl ($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, or the unsubstituted, mono- or di-substituted aryl groups phenyl or naphthyl, each of all of the afore-described aryl group substituents being $C_1$–$C_6$ alkyl or $C_1$–$C_6$ alkoxy. Alternatively, $R_1$ and $R_2$ together may form the group, =C(V)$_2$ or =C($R_6$)W, wherein W is —COOR$_5$ or —COR$_7$.

Preferably, $R_1$ is hydrogen, hydroxy or chloro and $R_2$ is the group, —CH(V)$_2$, wherein V is —CN or —COOR$_5$, and each $R_5$ is hydrogen, $C_1$–$C_4$ alkyl, phenyl($C_1$–$C_2$)alkyl, mono($C_1$-$C_4$)alkyl substituted phenyl($C_1$-$C_2$)alkyl, mono ($C_1$-$C_4$)alkoxy substituted phenyl($C_1$-$C_2$)alkyl or the unsubstituted or mono-substituted aryl groups phenyl or naphthyl, or $R_2$ is the group, —CH($R_6$)Y, wherein $R_6$ is hydrogen, $C_1$-$C_4$ alkyl or the unsubstituted or mono-substituted aryl groups phenyl or naphthyl, and Y is —COOR$_5$, —COR$_7$ or —CH$_2$OR$_8$, wherein $R_7$ is hydrogen, $C_1$-$C_4$ alkyl, the unsubstituted or mono-substituted aryl groups phenyl or naphthyl, amino, mono($C_1$-$C_4$) alkylamino, di($C_1$-$C_4$)alkylamino, phenylamino, mono- or di-($C_1$-$C_4$)alkyl substituted phenylamino, mono- or di-($C_1$-$C_4$)alkoxy substituted phenylamino, diphenylamino, mono- or di-($C_1$-$C_4$),alkyl substituted diphenylamino, mono- or di-($C_1$-$C_4$)alkoxy substituted diphenylamino, morpholino, or piperidino; $R_8$ is hydrogen, —COR$_5$, $C_1$-$C_4$ alkyl, $C_1$-$C_2$ alkoxy($C_1$-$C_4$)alkyl, phenyl($C_1$-$C_2$)alkyl, mono($C_1$-$C_4$)alkyl substituted phenyl($C_1$-$C_2$)alkyl, mono ($C_1$-$C_4$)alkoxy substituted phenyl($C_1$-$C_2$)alkyl or the unsubstituted or mono-substituted aryl groups phenyl or naphthyl, each of all of the aforedescribed aryl group substituents being $C_1$-$C_4$ alkyl or $C_1$-$C_4$ alkoxy.

More preferably, $R_1$ is hydrogen, hydroxy or chloro and $R_2$ is the group, —CH(V)$_2$, wherein V is CN, or $R_2$ is the group, —CH($R_6$)Y, wherein $R_6$ is hydrogen or $C_1$-$C_4$ alkyl, and Y is —COOR$_5$ or —CH$_2$OR$_8$, wherein $R_5$ is hydrogen or $C_1$-$C_4$ alkyl, and $R_8$ is hydrogen, —COR$_5$ or $C_1$-$C_4$ alkyl. Alternatively, $R_1$ and $R_2$ together form the group, =C(V)$_2$ or =C($R_6$)W, wherein W is —COOR$_5$.

In graphic formula I, $R_3$ and $R_4$ may each be $C_1$-$C_6$ alkyl, $C_1$-$C_6$ alkoxy, chloro or fluoro, and m and n are each the integers 0, 1, or 2. Preferably, $R_3$ and $R_4$ are each $C_1$-$C_4$ alkyl, $C_1$-$C_4$ alkoxy, chloro or fluoro, and m and n are each the integers 0 or 1. Most preferably, $R_3$ and $R_4$ are each $C_1$-$C_3$ alkyl or $C_1$-$C_3$ alkoxy, and m and n are each the integers 0 or 1.

B and B' in graphic formula I may each be selected from the group consisting of: (i) the unsubstituted, mono-, di-, and tri-substituted aryl groups, phenyl and naphthyl; (ii) the unsubstituted, mono- and di-substituted aromatic heterocyclic groups pyridyl, furanyl, benzofuran-2-yl, benzofuran-3-yl, thienyl, benzothien-2-yl and benzothien-3-yl, each of said aryl and aromatic heterocyclic substituents in parts (i) and (ii) being selected from the group consisting of hydroxy, amino, mono($C_1$-$C_6$)alkylamino, di($C_1$-$C_6$)alkylamino, piperidino, morpholino, pyrryl, $C_1$-$C_6$ alkyl, $C_1$-$C_6$ chloroalkyl, $C_1$-$C_6$ fluoroalkyl, $C_1$-$C_6$ alkoxy, mono($C_1$-$C_6$) alkoxy($C_1$-$C_4$)alkyl, acryloxy, methacryloxy, chloro and fluoro; (iii) the groups represented by the following graphic formulae:

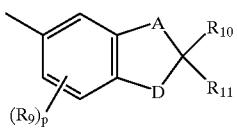

IIA

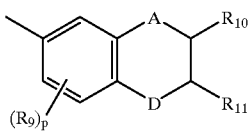

IIB wherein A may be carbon or oxygen and D may be oxygen or substituted nitrogen, provided that when D is substituted nitrogen, A is carbon, said nitrogen substituents being selected from the group consisting of hydrogen, $C_1$-$C_6$ alkyl and $C_2$-$C_6$ acyl; each $R_9$ is $C_1$-$C_6$ alkyl, $C_1$-$C_6$ alkoxy, hydroxy, chloro or fluoro; $R_{10}$ and $R_{11}$ are each hydrogen or $C_1$-$C_6$ alkyl; and p is the integer 0, 1 or 2; (iv) $C_1$-$C_6$ alkyl, $C_1$-$C_6$ chloroalkyl, $C_1$-$C_6$ fluoroalkyl, $C_1$-$C_6$ alkoxy ($C_1$-$C_4$)alkyl, $C_3$-$C_6$ cycloalkyl, mono($C_1$-$C_6$) alkoxy ($C_3$-$C_6$)cycloalkyl, mono($C_1$-$C_6$)alkyl($C_3$-$C_6$)cycloalkyl, chloro($C_3$-$C_6$)cycloalkyl and fluoro($C_3$-$C_6$)cycloalkyl; and (v) the group represented by the following graphic formula:

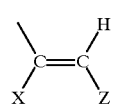

IIC wherein X in graphic formula IIC may be hydrogen or $C_1$-$C_4$ alkyl and Z in graphic formula IIC may be selected from the unsubstituted, mono-, and di-substituted members of the group consisting of naphthyl, phenyl, furanyl and thienyl, each of said group substituents in this part (v) being $C_1$-$C_4$ alkyl, $C_1$-$C_4$ alkoxy, fluoro or chloro; or (vi) B and B' taken together form fluoren-9-ylidene, mono-, or di-substituted fluoren-9-ylidene or form a member selected from the group consisting of saturated $C_3$-$C_{12}$ spiro-monocyclic hydrocarbon rings, e.g., cyclopropylidene., cyclobutylidene, cyclopentylidene, cyclohexylidene, cycloheptylidene, cyclooctylidene, cyclononylidene, cyclodecylidene cycloundecylidene and cyclododecylidene; saturated $C_7$-$C_{12}$ spiro-bicyclic hydrocarbon rings, e.g., bicyclo [2.2.1]heptylidene, i.e., norbornylidene, 1,7,7-trimethyl bicyclo[2.2.1]heptylidene, i.e., bornylidene, bicyclo[3.2.1] octylidene, bicyclo[3.3.1]nonan-9-ylidene and bicyclo [4.3.2]undecane, and saturated $C_7$-$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$-$C_4$ alkyl, $C_1$-$C_4$ alkoxy, fluoro and chloro.

More preferably, B and B' are each selected from the group consisting of: (i) phenyl, mono-substituted phenyl and di-substituted phenyl, preferably substituted in the meta and/or para positions; (ii) the unsubstituted, mono- and di-substituted aromatic heterocyclic groups furanyl, benzofuran-2-yl, thienyl and benzothien-2-yl, each of said phenyl and aromatic heterocyclic substituents being selected from the group consisting of hydroxy, amino, mono($C_1$-$C_3$) alkylamino, di($C_1$-$C_3$)alkylamino, piperidino, morpholino, pyrryl, $C_1$-$C_3$ alkyl, $C_1$-$C_3$ chloroalkyl, $C_1$-$C_3$ fluoroalkyl, $C_1$-$C_3$ alkoxy, mono($C_1$-$C_3$)alkoxy($C_1$-$C_3$)alkyl, fluoro and chloro; (iii) the groups represented by the graphic formulae IIA and IIB, wherein A is carbon and D is oxygen, $R_9$ is $C_1$-$C_3$ alkyl or $C_1$-$C_3$ alkoxy, $R_{10}$ and $R_{11}$ are each hydrogen or $C_1$-$C_4$ alkyl; and p is the integer 0 or 1; (iv) $C_1$-$C_4$ alkyl; and (v) the group represented by the graphic formula IIC wherein X is hydrogen or methyl and Z is phenyl or mono-substituted phenyl, said phenyl substituent being selected from the group consisting of $C_1$-$C_3$ alkyl, $C_1$-$C_3$ alkoxy and fluoro; or (vi) B and B' taken together form fluoren-9-ylidene, mono-substituted fluoren-9-ylidene or a member selected from the group consisting of saturated $C_3$-$C_8$ spiro-monocyclic hydrocarbon rings saturated $C_7$-$C_{10}$ spiro-bicyclic hydrocarbon rings, and saturated $C_7$-$C_{10}$ spiro-tricyclic hydrocarbon rings, said fluoren-9-ylidene substituent being selected from the group consisting of $C_1$-$C_3$ alkyl, $C_1$-$C_3$ alkoxy, fluoro and chloro.

Most preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl and benzothien-2-yl, each of said phenyl and aromatic heterocyclic substituents being selected from the group consisting of hydroxy, $C_1$–$C_3$ alkyl, $C_1$–$C_3$ alkoxy, fluoro and chloro; and (iii) the group represented by graphic formula IIA, wherein A is carbon and D is oxygen, $R_9$ is $C_1$–$C_3$ alkyl or $C_1$–$C_3$ alkoxy, $R_{10}$ and $R_{11}$ are each hydrogen or $C_1$–$C_3$ alkyl, and p is the integer 0 or 1; or (iv) B and B' taken together form fluoren-9-ylidene, adamantylidene, bornylidene, norbornylidene or bicyclo[3.3.1]nonan-9-ylidene.

Compounds represented by graphic formula I having the substituents $R_3$, $R_4$, B, and B', described hereinbefore, may be prepared by the following described Reactions A through D. Methods for the preparation of compounds represented by graphic formula I and including the substituents $R_1$ and $R_2$, described hereinbefore, may be prepared by the following described Reaction E. Compounds represented by graphic formula V, VA, or VB (as shown in Reactions A, B and C respectively) are either purchased or prepared by Friedel-Crafts methods shown in Reaction A using an appropriately substituted or unsubstituted benzoyl chloride of graphic formula IV with a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B or VB in Reaction C). R and R' represent some of the possible substituents described hereinbefore as $R_3$ and $R_4$ in graphic formula I.

REACTION A

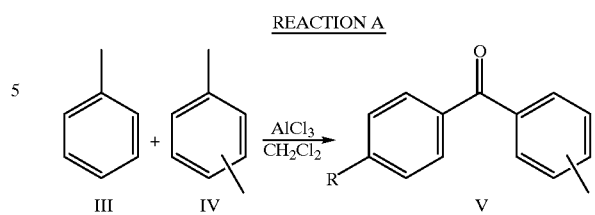

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound. Propargyl alcohols having a B or B' group represented by graphic formula IIC may be prepared by the methods described in U.S. Pat. No. 5,274,132, column 2, lines 40 to 68.

REACTION B

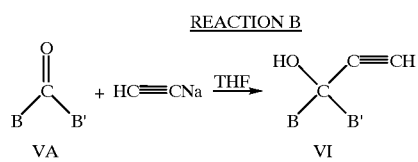

In Reaction C, a substituted or unsubstituted benzophenone represented by graphic formula VB is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. If $R_3$ and $R_4$ on the benzophenone are not identical, i.e., not structurally symmetrical, a mixture of cis and trans half esters will be formed that will require further purification to isolate a distinct isomer. The half ester (VIII) undergoes cyclodehydration in the presence of acetic anhydride to form the acetoxynaphthalene represented by graphic formula IX. This product is hydrolyzed in an aqueous alcoholic solution of base, such as sodium hydroxide, followed by treatment with aqueous hydrochloric acid ($H^+$) to form the carboxynaphthol represented by graphic formula X.

REACTION C

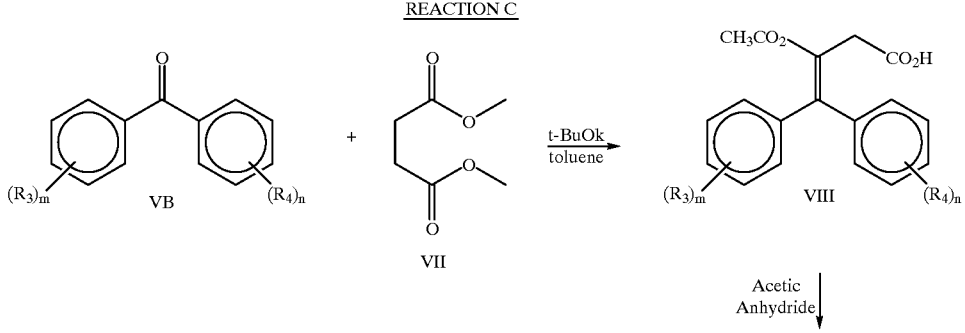

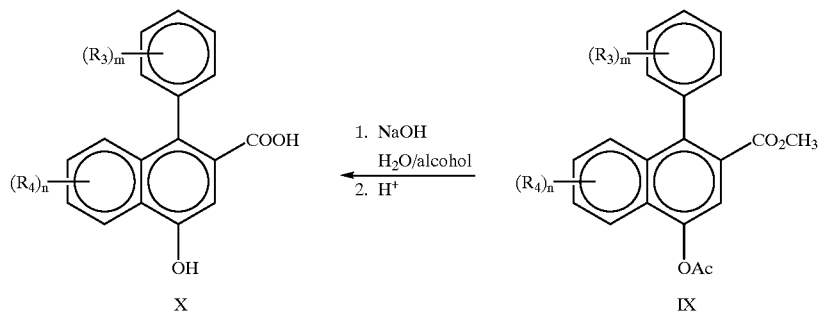

In Reaction D, the carboxynaphthol represented by graphic formula X is cyclized by mixing with concentrated sulfuric acid at a temperature of 0–4° C. to form a hydroxy-substituted benz-fused fluorenone represented by graphic formula XI. See the article by F. G. Baddar et al, in the J. Chem. Soc., page 986, 1958. Alternate methods of synthesizing the compound represented by graphic formula XI are described by C. F. Koelsch in the Journal of Organic Chemistry, volume 26, page 2590, 1961 and by M. Vancurova, et al, in Ceskoslovenska Farmacie, Vol. 31, No. 8, pp 308–310, October, 1982.

Coupling of the compound represented by graphic formula XI with a propargyl alcohol represented by graphic formula VI in the presence of a catalytic amount of an acid, e.g., dodecylbenzene sulfonic acid (DBSA), results in the indeno-fused naphthopyran represented by graphic formula IA.

REACTION D

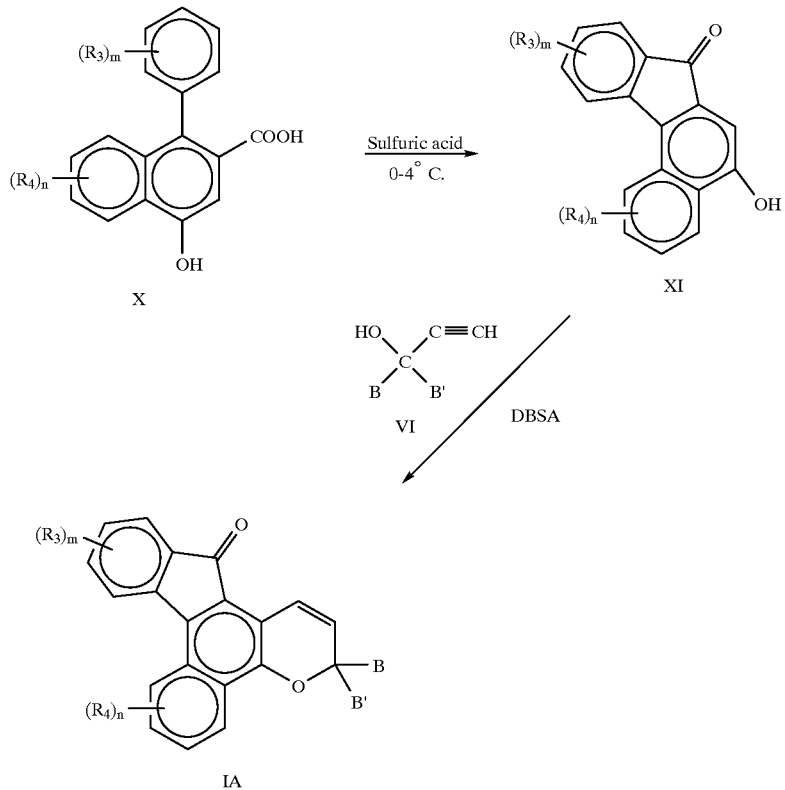

In Reaction E, further methods for preparing compounds represented by graphic formula I having a variety of $R_1$ and $R_2$ substituents are described. Starting with the compound represented by graphic formula IA, treatment with an α-bromoester of graphic formula XII in the presence of activated zinc dust results in the compound represented by graphic formula IB. This reaction, referred to as the Reformatsky Reaction, is reviewed by R. L. Shriner in *Organic Reactions* Vol.1, pp 1–37, 1942. The compound represented by graphic formula IB can be further reacted with chlorinating reagents, for example thionyl chloride to produce derivatives represented by graphic formula IC. The compound represented by graphic formula IC can be dehydrohalogenated by heating in the presence of a tertiary amine, for example collidine, to yield α,β-unsaturated esters of graphic formula ID.

Alternatively the compound represented by graphic formula IA can be condensed with a compound containing an active methylene represented by graphic formula XIII in the presence of an amine to produce the compound represented by graphic formula IE. This reaction, referred to as the Knoevenagel Condensation, is reviewed by G. Jones in *Organic Reactions* Vol. 15, pp 204–599, 1967.

plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from orange to blue/gray.

REACTION E

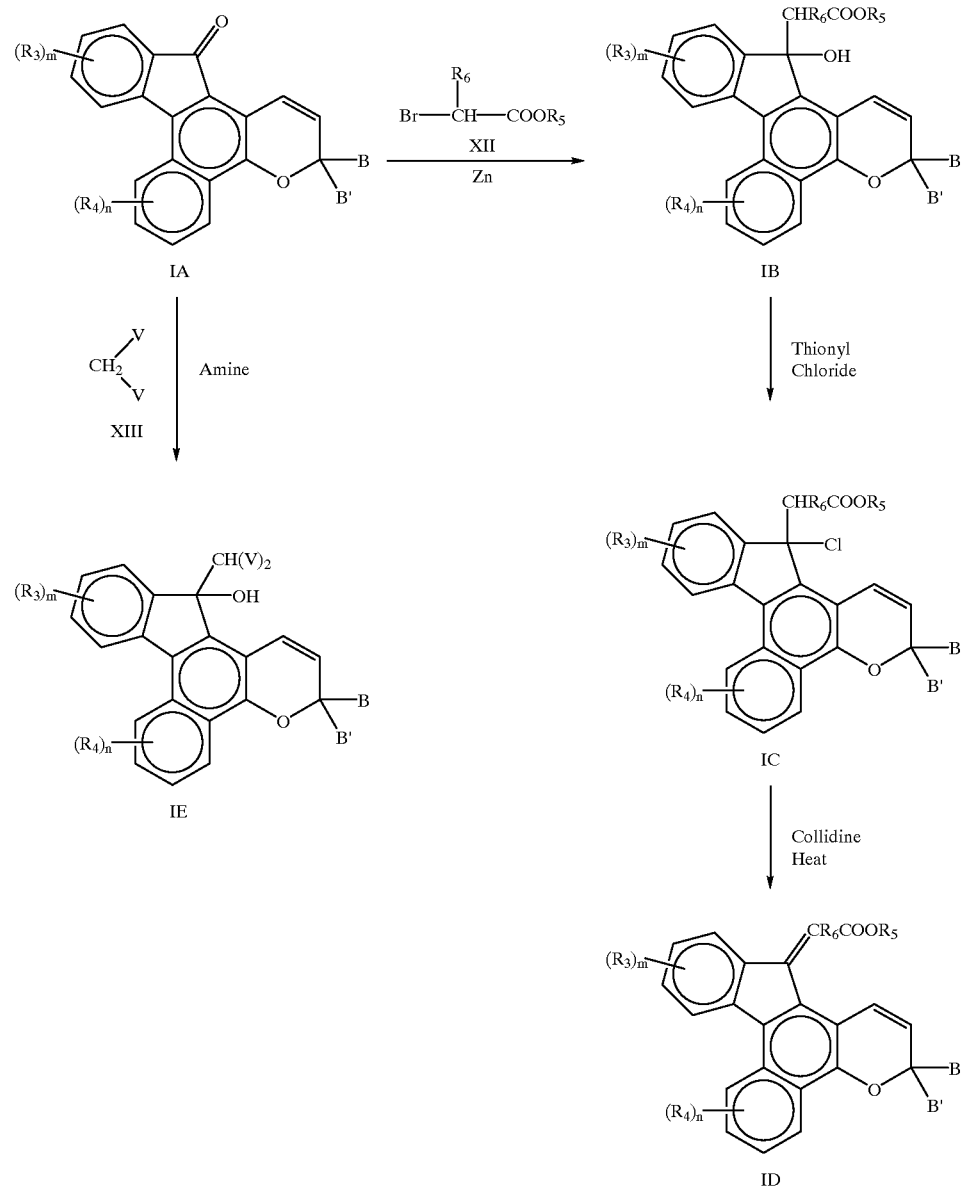

Compounds represented by graphic formula I, IA, IB, IC, ID and IE may be used in those applications in which organic photochromic substances may be employed, such as optical lenses, e.g., vision correcting ophthalmic lenses and Examples of contemplated naphthopyran compounds within the scope of the invention are the following:

(a) 3,3-diphenyl-13-hydroxy-13-(2-oxo-2-ethoxyethyl)-1H-indeno[2,1-f]naphtho[1,2-b]pyran;

(b) 3,3-diphenyl-13-chloro-13-(2-oxo-2-ethoxyethyl)-1H-indeno[2,1-f]naphtho[1,2-b]pyran;

(c) 3,3-di(4-methoxyphenyl)-6,11-dimethyl-13-hydroxy-13-(2-oxo-2-ethoxyethyl)-1H-indeno[2,1-f]naphtho[1,2-b]pyran;

(d) 3-(4-methylphenyl)-3-(4-fluorophenyl)-13-chloro-13-(2-oxo-2-ethoxyethyl)-1H-indeno[2,1-f]naphtho[1,2-b]pyran;

(e) 3-(4-methoxyphenyl)-3-(2,3-dihydrobenzofur-5-yl)-6,11-difluoro-13-hydroxy-13-(2-oxo-2-ethoxyethyl)-1H-indeno[2,1-f]naphtho[1,2-b]pyran;

(f) 3-phenyl-3-(4-morpholinophenyl)-13-hydroxy-13-(1-oxo-2-methoxyprop-2-yl)-1H-indeno[2,1-f]naphtho[1,2-b]pyran; and (g) 3-phenyl-3-(4-morpholinophenyl)-6,11-dimethyl-13-chloro-13-(1-carboxyethyl)-1H-indeno[2,1-f]naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than in the operating examples, or where otherwise indicated, all numbers expressing wavelengths, quantities of ingredients or reaction conditions used herein are to be understood as modified in all instances by the term "about".

Examples of complementary organic photochromic compounds include other naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)-benzoxazines, and mixtures of such photochromic compounds.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0–280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol methacrylate monomers and alkoxylated polyhydric alcohol acrylate monomers, such as ethoxylated trimethylol propane triacrylate monomers; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene dimethacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE 1

Step 1

Potassium t-butoxide (24.6 grams, 0.22 mole) was added to a reaction flask containing 100 milliliters (mL) of anhydrous toluene. The reaction flask was equiped with an overhead stirrer, dropping funnel, and a condenser with nitrogen inlet. A mixture of benzophenone (36.4 grams, 0.2 mole), dimethyl succinate (29.2 grams, 0.2 mole) and toluene (350 grams) was added to the reaction flask over a period of one-half hour with stirring. The reaction mixture was stirred for 16 hours. About 200 mL of water was added to the resulting pasty mixture and mixed well. The aqueous layer was separated, washed with toluene, acidified to pH 2 with dilute hydrochloric acid, extracted into toluene, and dried over magnesium sulfate. The solvents, toluene and residual t-butanol, were removed and the product was recrystallized from diethyl ether/hexane. The recovered product, 42.86 grams, had a melting point of 65° C. and a nuclear magnetic resonance spectrum (NMR) showing the product to have a structure consistent with the Stobbe half-ester: 4,4-diphenyl-3-methoxycarbonyl-3-butenoic acid.

Step 2

The half-ester (41.4 grams, 0.14 mole) from Step 1 was added to a reaction flask containing acetic anhydride (70 mL, 0.75 mole) and sodium acetate (16 grams, 0.2 mole) and the mixture was refluxed for 6 hours. Excess acetic anhydride was removed under reduced pressure before adding water. The resulting solution was extracted into toluene and dried. The solvent, toluene, was removed and the resulting residue was washed with a 50:50 mixture of toluene:methanol. The resulting product was recrystallized from diethyl ether/hexane. The recovered product, 40.16 grams, had a melting point of 86° C. and a nuclear magnetic resonance spectrum (NMR) showed the product to have a structure consistent with the methyl ester of 4-acetoxy-1-phenyl-2-naphthoic acid.

Step 3

The ester (40 grams, 0.125 mole) from Step 2 was added to a reaction flask containing 300 mL of a 10 weight percent solution of aqueous sodium hydroxide and refluxed for 18 hours. Afterwards, 5 M hydrochloric acid was added to acidify the reaction mixture to pH 6. The resulting mixture was cooled and the solids were removed by filtration. The recovered solid was washed with hexane and dried in an oven maintained at 80° C. for 72 hours. The recovered product, 31.45 grams, had a melting point of 208° C. and a nuclear magnetic resonance spectrum (NMR) showing the product to have a structure consistent with 4-hydroxy-1-phenyl-2-naphthoic acid.

Step 4

The 4-hydroxy-1-phenyl-2-naphthoic acid, 13.2 grams, from Step 3, was added in portions with vigorous mixing to a reaction flask containing 140 mL of concentrated sulfuric acid maintained at about 40° C. The mixture became green in color immediately. The reaction mixture was then poured into a beaker containing approximately 250 mL of ice water cold and stirred for 30 minutes. The color of the reaction mixture turned a red/purple color and a solid formed. The solid was collected by filtration, recrystallized from diethyl ether/hexane, washed with 10 percent diethyl ether/hexane, and dried at 82° C. for 72 hours. The recovered product, 10.33 grams, had a melting point of 256° C. and a nuclear magnetic resonance spectrum (NMR) showing the product to have a structure consistent with 5-hydroxy-7H-benzo[c]fluoren-7-one.

Step 5

5-Hydroxy-7H-benzo [c]fluoren-7-one (8 grams), from Step 4, was added to a reaction flask containing 1,1-diphenyl-2-propyn-1-ol (7.3 grams) and 75 mL of toluene. The resulting mixture was stirred and heated to 50° C., three drops of dodecybenzene sulfonic acid were added, and the reaction mixture was kept at 50° C. for 6 days. After the reaction mixture cooled to room temperature, it was filtered and the collected filtrate was washed with 5 weight percent aqueous sodium hydroxide until the washings were colorless. The residual solid was washed with a 10:1 solvent mixture of ether:acetone, dissolved in chloroform and recrystallized from chloroform/hexane. The recovered product, 7.18 grams, had a melting point of 254° C. and a nuclear magnetic resonance spectrum (NMR) showing the product to have a structure consistent with 3,3-diphenyl-13-oxo-1H-indeno[2,1-f]naphtho [1,2-b]pyran.

Step 6

3,3-Diphenyl-13-oxo-1H-indeno[2,1-f]naphtho[1,2-b] pyran (0.435 gram) from Step 5, and ethyl bromoacetate (0.3 gram) were added to a reaction flask containing 20 mL of anhydrous ether, 20 mL of anhydrous tetrahydrofuran and 50 mL of toluene. The resulting reaction mixture was added dropwise to gently warmed zinc powder (0.163 gram) with stirring under nitrogen. Afterwards, the reaction mixture was refluxed for 45 minutes, during which time the solution color changed from red to gray. The reaction was cooled, 10 weight percent aqueous sulfuric acid (10 mL) and chloroform (50 mL) were added and the organic phase was separated. The organic phase was washed with water, dried and recrystallized from chloroform/hexane. The recovered product, 0.496 gram, had a melting point of 163° C. and a nuclear magnetic resonance spectrum (NMR) showing the product to have a structure consistent with 3,3-diphenyl-13-hydroxy-13-(2-oxo-2-ethoxyethyl)-1H-indeno[2,1-f]naphtho[1,2-b] pyran.

Comparative Example 1

Step 1

Potassium t-butoxide (75 grams, 0.67 mole) was added to a reaction flask containing 200 milliliters (mL) of toluene. The reaction flask was equiped with an overhead stirrer, dropping funnel, and a condenser with nitrogen inlet. The contents of the reaction flask was heated to reflux temperature and a mixture of benzophenone (91 grams, 0.5 mole), dimethyl succinate (90 grams, 0.62 mole), and toluene (100 grams) was added over a period of one-half hour. The resulting pasty mixture was refluxed an additional two hours, cooled, and about 400 mL of water was added and mixed well. The aqueous layer was separated, acidified with dilute hydrochloric acid, and extracted with 200 mL of toluene. The solvents, toluene and residual t-butanol, were removed on the rotary evaporator to produce a near quantitative yield of crude Stobbe half-ester: 4,4-diphenyl-3-methoxycarbonyl-3-butenoic acid. This material was not purified further but was used directly in the next step.

Step 2

The crude half-ester from Step 1 was added to a reaction flask containing 200 mL of toluene. Acetic anhydride (100 grams) and anhydrous sodium acetate (15 grams) were added and the mixture was refluxed for 17 hours. The mixture was cooled and the solvent, toluene, was removed on a rotary evaporator. The resulting residue was dissolved in 200 mL of methylene chloride and stirred. Water (200 mL) was added followed by the slow addition of solid sodium carbonate until carbon dioxide evolution ceased. The methylene chloride layer was separated and washed with water. The solvent, methylene chloride, was removed on a rotary evaporator to yield a viscous oil, containing primarily 1-phenyl-2-methoxycarbonyl-4-acetoxy-naphthalene. This material was not purified further but was used directly in the next step.

Step 3

The oil containing 1-phenyl-2-methoxycarbonyl-4-acetoxy-naphthalene from Step 2 was added to a reaction flask containing 400 mL of methanol. Two mL of concentrated hydrochloric acid was added and the mixture was heated to reflux. After approximately four hours, the volume of the mixture was reduced by half on a rotary evaporator. As the mixture cooled, the product started to crystallize. The resulting crystals were suction filtered, washed with fresh methanol, and dried. The recovered product, 100 grams, had a melting point of 174–176° C. and a nuclear magnetic resonance spectrum (NMR) showing the product to have a structure consistent with 4-phenyl-3-methoxycarbonyl-1-naphthol.

Step 4

4-Phenyl-3-methoxycarbonyl-1-naphthol (2 grams) from Step 3 and 1,1-diphenyl-2-propyn-1-ol (2 grams) were added to a reaction flask containing 100 milliliters (mL) of toluene. The resulting mixture was stirred and heated to 40° C., two drops of dodecylbenzene sulfonic acid were added, and the reaction mixture was kept at 40° C. for three hours. After the reaction mixture cooled to room temperature, it was added to an equal volume of water. The organic layer was separated and the solvent, toluene, was removed on a rotary evaporator. The resulting residue was chromatographed on silica using a 2:1 mixture of hexane:ethyl acetate as the eluant. The photochromic fractions were combined, the solvent was evaporated, and the desired product was induced to crystallize from a hexane/diethyl ether mixture. The recovered crystals were dried and filtered to yield 2 grams of product having a melting point of 152–153° C. An NMR spectrum showed the product to have a structure consistent with 2,2-diphenyl-5-methoxycarbonyl-6-phenyl-[2H]-naphtho[1,2-b]pyran.

EXAMPLE 2

Part A

Testing was done with the Example 1 and Comparative Example 1 photochromic naphthopyrans incorporated into polymeric samples by the following method. The quantity of naphthopyran calculated to yield a 1.5 times $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl proprionitrile) (AIBN). The naphthopyran was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven set to increase the temperature from 40° C. to 95° C. over a 5 hour interval, hold the temperature at 95° C. for 3 hours and then lower it to 60° C., for at least 2 hours before the end of the curing cycle. After the mold was opened, the polymer sheet was cut using a diamond blade saw into 2 inch (5.1 centimeters) test squares.

Part B

The photochromic test squares of Part A were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach the photochromic compounds. The test squares were then cooled to room temperature, exposed to fluorescent room lighting for at least 2 hours and then kept covered for at least 2 hours prior to testing on an optical bench maintained at 75° F. (23.90° C.).

The optical bench comprises a 150 watt Xenon arc lamp, a tungsten lamp, power supplies for both lamps, condensing lenses as needed to maintain collimated light beams from both lamps, a remote controlled shutter, a copper sulfate bath acting as a heat sink for the arc lamp, a Schott WG-320 nm cut-off filter which removes short wavelength radiation, neutral density filter(s), a sample holder in which the sample to be tested is inserted, a photopic filter, light detector, and radiometer assembly, a strip chart recorder, and a means for maintaining the alignment of the aforestated components during testing.

Change in optical density ($\Delta$ OD) of a sample was determined by inserting a photochromic test sample in the bleached state into the sample holder, adjusting the transmittance scale to 100%, opening the shutter from the Xenon lamp to provide ultraviolet radiation to change the sample from the bleached state to an activated (darkened) state, measuring the transmittance through the sample. The transmittance was measured by directing a beam of light from the tungsten lamp at a small angle normal to the surface of the sample, through the sample, and to a photopic filter, light detector and radiometer assembly. The photopic filter passes wavelengths such that the detector mimics the response of the human eye and produces output signals that are processed by the radiometer. The change in optical density was calculated according to the formula $\Delta$ OD=log(100/%Ta) where %Ta is the percent transmittance in the activated state and the logarithm is to the base 10.

The $\Delta$ OD/Min, which represents the sensitivity of the photochromic compound's response to UV light, was measured over the first five (5) seconds of UV exposure, then expressed on a per minute basis. The saturation optical density (OD) was taken under identical conditions as the $\Delta$ OD/Min, except UV exposure was continued for 20 minutes. The lambda max (Vis) is the wavelength in the visible spectrum at which the maximum absorption of the activated (colored) form of the photochromic compound in the test square occurs. The bleach rate (T ½) is the time interval in seconds for the absorbance of the activated form of the naphthopyran in the test squares to reach one half the highest absorbance at room temperature (75° F., 23.9° C.) after removal of the source of activating light. Results for the compounds of the Examples are tabulated in Table 1.

Part C

The photochromic test square polymerizates of Example 1 and Comparative Example 1 prepared in Part A were tested in a UV/Visible spectrophotometer to determine the lambda ($\lambda$) max (Vis) and the lambda max (UV) wavelengths. The lambda max (Vis) is the wavelength of the visible spectrum at which the maximum absorption of the activated (colored) form of the photochromic compound in a test square occurs. The lambda max (UV) is the wavelength of the ultraviolet range closest to the visible spectrum at which the absorption of the photochromic compound occurs. These results are reported in Table 2.

The molal absorptivity or molal extinction coefficient ($\epsilon$) reported in Table 2 is equal to the absorbance of the photochromic compound in a test square at the $\lambda$ max in the UV (A) divided by the thickness of the test square in centimeters (b) multiplied by the concentration of the photochromic compound in the test square in moles per kilogram (m) according to the formula: $\epsilon = A/bm$

TABLE 1

| Compound Example | Sensitivity $\Delta$OD/min | $\Delta$OD @ Saturation | Bleach Rate T ½ (sec) |
|---|---|---|---|
| 1 | 0.34 | 1.0 | 338 |
| CE 1 | 0.19 | 0.68 | 230 |

The data presented in Table 1 show that the compound of Example 1, in comparison to Comparative Example (CE) 1, has greater sensitivity, i.e., coloration rate, a higher $\Delta$ OD at saturation, i.e., activated intensity, and an acceptable bleach rate, i.e., fade rate.

TABLE 2

| Compound Example | $\lambda$ max (nm) UV | Molal Absorpt. ($\epsilon$) | $\lambda$ max (nm) Vis (minor) | $\lambda$ max (nm) Vis (major) |
|---|---|---|---|---|
| 1 | 360 | 12,218 | 425 | 536 |
| CE 1 | 346 | 5709 | 407 | 482 |

The data presented in Table 2 show that the compound of Example 1, in comparison to CE 1, has a higher $\lambda$ max UV and $\lambda$ max Vis of the major peak which demonstrates a bathochromic shift in the UV and visible spectra, and a higher molal absorptivity or molal coefficient of extinction ($\epsilon$) in the UV spectrum.

The present invention has been described with reference to specific details of particular embodiments thereof. It is not intended that such details be regarded as limitations upon the scope of the invention except insofar as to the extent that they are included in the accompanying claims.

We claim:
1. A naphthopyran compound represented by the following graphic formula:

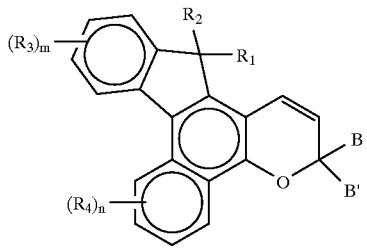

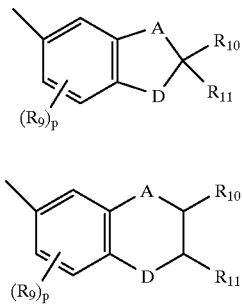

wherein,
(a) $R_1$ is hydrogen, hydroxy or chloro and $R_2$ is the group, —CH(V)$_2$, wherein V is —CN or —COOR$_5$, and each $R_5$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl or the unsubstituted, mono- or di-substituted aryl groups phenyl or naphthyl, or $R_2$ is the group, —CH($R_6$)Y, wherein $R_6$ is hydrogen, $C_1$–$C_6$ alkyl or the unsubstituted, mono- or di-substituted aryl groups phenyl or naphthyl, and Y is —COOR$_5$, —COR$_7$, or —CH$_2$OR$_8$, wherein $R_7$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, or piperidino; $R_8$ is hydrogen, —COR$_5$, $C_1$–$C_6$ alkyl, $C_1$–$C_3$ alkoxy ($C_1$–$C_6$)alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, each of all of said aryl group substituents being $C_1$–$C_6$ alkyl or $C_1$–$C_6$ alkoxy; or
(b) $R_1$ and $R_2$ together form the group, =C(V)$_2$ or =C($R_6$)W, wherein W is —COOR$_5$ or —COR$_7$;
(c) $R_3$ and $R_4$ are each $C_1$–$C_6$ alkyl, $C_1$–$C_6$ alkoxy, chloro, or fluoro, and m and n are each the integers 0, 1, or 2
(d) B and B' are each selected from the group consisting of:
 (i) the unsubstituted, mono-, di-, and tri-substituted aryl groups, phenyl and naphthyl;
 (ii) the unsubstituted, mono-, and di-substituted aromatic heterocyclic groups pyridyl, furanyl, benzofuran-2-yl, benzofuran-3-yl, thienyl, benzothien-2-yl and benzothien-3-yl, said aryl and aromatic heterocyclic substituents in (d) (i) and (ii) being selected from the group consisting of hydroxy, amino, mono($C_1$–$C_6$)alkylamino, di($C_1$–$C_6$)alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, chloro and fluoro;
 (iii) the groups represented by the following graphic formulae:

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl and $C_2$–$C_6$ acyl; each $R_9$ is $C_1$–$C_6$ alkyl, $C_1$–$C_6$ alkoxy, hydroxy, chloro or fluoro; $R_{10}$ and $R_{11}$ are each hydrogen or $C_1$–$C_6$ alkyl; and p is the integer 0, 1 or 2;
 (iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)-cycloalkyl, chloro ($C_3$–$C_6$)cycloalkyl and fluoro($C_3$–$C_6$)cyclo-alkyl; and
 (v) the group represented by the following graphic formula:

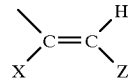

wherein X is hydrogen or $C_1$–$C_4$ alkyl and Z is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, fluoro or chloro; or
 (vi) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein,
(a) $R_1$ is hydrogen, hydroxy or chloro and $R_2$ is the group, —CH(V)$_2$, wherein V is —CN or —COOR$_5$, and each $R_5$ is hydrogen, $C_1$–$C_4$ alkyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl or the unsubstituted or mono-substituted aryl groups phenyl or naphthyl, or $R_2$ is the group, —CH($R_6$)Y, wherein $R_6$ is hydrogen, $C_1$–$C_4$ alkyl or the unsubstituted or mono-substituted aryl groups phenyl or naphthyl, and Y is —COOR$_5$, —COR$_7$, or —CH$_2$OR$_8$, wherein $R_7$ is hydrogen, $C_1$–$C_4$ alkyl, the unsubstituted or mono-substituted aryl groups phenyl or naphthyl, amino, mono($C_1$–$C_4$)alkylamino, di($C_1$–$C_4$) alkylamino, phenylamino, mono- or di-($C_1$–$C_4$)alkyl substituted phenylamino, mono- or di-($C_1$–$C_4$)alkoxy substituted phenylamino, diphenylamino, mono- or di- ($C_1$–$C_4$)alkyl substituted diphenylamino, mono- or di-($C_1$–$C_4$)alkoxy substituted diphenylamino, morpholino or piperidino; $R_8$ is hydrogen, —$COR_5$, $C_1$–$C_4$ alkyl, $C_1$–$C_2$ alkoxy($C_1$–$C_4$)alkyl, phenyl($C_1$–$C_2$)alkyl, mono ($C_1$–$C_4$)alkyl substituted phenyl($C_1$–$C_2$)alkyl, mono ($C_1$–$C_4$)alkoxy substituted phenyl($C_1$–$C_2$)alkyl or the unsubstituted or mono-substituted aryl groups phenyl or naphthyl, each of all of said aryl group substituents being $C_1$–$C_4$ alkyl or $C_1$–$C_4$ alkoxy; or (b) $R_1$ and $R_2$ together form the group, =$C(V)_2$ or =$C(R_6)W$, wherein W is —$COOR_5$ or —$COR_7$;

(c) $R_3$ and $R_4$ are each $C_1$–$C_4$ alkyl, $C_1$–$C_4$ alkoxy, chloro or fluoro, and m and n are each the integers 0 or 1;

(d) B and B' are each selected from the group consisting of:
(i) phenyl, mono-substituted phenyl and di-substituted phenyl;
(ii) the unsubstituted, mono-, and di-substituted aromatic heterocyclic groups furanyl, benzofuran-2-yl, thienyl and benzothien-2-yl, said phenyl and aromatic heterocyclic substituents in (d)(i) and (ii) being selected from the group consisting of hydroxy, amino, mono($C_1$–$C_3$)alkyl-amino, di($C_1$–$C_3$) alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;
(iii) the groups represented by the following graphic formulae:

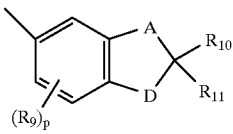

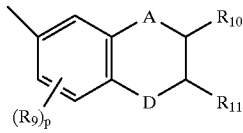

wherein A is carbon and D is oxygen, $R_9$ is $C_1$–$C_3$ alkyl or $C_1$–$C_3$ alkoxy, $R_{10}$ and $R_{11}$ are each hydrogen or $C_1$–$C_4$ alkyl; and p is the integer 0 or 1;
(iv) $C_1$–$C_4$ alkyl; and
(v) the group represented by the following graphic formula:

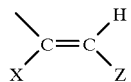

wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro; or
(vi) B and B' taken together form a fluoren-9-ylidene, mono-substituted fluoren-9-ylidene or a member selected from the group consisting of saturated $C_3$–$C_8$ spiro-monocyclic hydrocarbon rings saturated $C_7$–$C_{10}$ spiro-bicyclic hydrocarbon rings, and saturated $C_7$–$C_{10}$ spiro-tricyclic hydrocarbon rings, each of said fluoren-9-xylidene substituents being selected from the group consisting of $C_1$–$C_3$ alkyl, $C_1$–$C_3$ alkoxy, fluoro and chloro.

3. The naphthopyran compound of claim 2 wherein,
(a) $R_1$ is hydrogen, hydroxy or chloro and $R_2$ is the group, —$CH(V)_2$, wherein V is —CN, or $R_2$ is the group, —$CH(R_6)Y$, wherein $R_6$ is hydrogen or $C_1$–$C_4$ alkyl, and Y is —$COOR_5$ or —$CH_2OR_8$, wherein $R_5$ is hydrogen or $C_1$–$C_4$ alkyl, $R_8$ is hydrogen, —$COR_5$ or $C_1$–$C_4$ alkyl; or
(b) $R_1$ and $R_2$ together form the group =$C(V)_2$ or =$C(R_6)W$, wherein W is —$COOR_5$;
(c) $R_3$ and $R_4$ are each $C_1$–$C_3$ alkyl or $C_1$–$C_3$ alkoxy, and m and n are each the integers 0 or 1; and
(d) B and B' are each selected from the group consisting of phenyl, mono-, and di-substituted phenyl, unsubstituted, mono-, and di-substituted aromatic heterocyclic groups furanyl, benzofuran-2-yl, thienyl and benzothien-2-yl, each of said phenyl and aromatic heterocyclic substituents being selected from the group consisting of hydroxy, $C_1$–$C_3$ alkyl, $C_1$–$C_3$ alkoxy, fluoro and chloro; and the group represented by the following graphic formula:

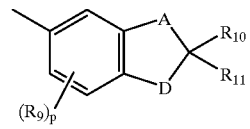

wherein A is carbon and D is oxygen, $R_9$ is $C_1$–$C_3$ alkyl or $C_1$–$C_3$ alkoxy, $R_{10}$ and $R_{11}$ are each hydrogen or $C_1$–$C_3$ alkyl, and p is the integer 0 or 1; or B and B' taken together form fluoren-9-ylidene, adamantylidene, bornylidene, norbornylidene or bicyclo(3.3.1)nonan-9-ylidene.

4. A naphthopyran compound selected from the group consisting of:
(a) 3,3-diphenyl-13-hydroxy-13-(2-oxo-2-ethoxyethyl)-1H-indeno[2,1-f]naphtho[1,2-b]pyran;
(b) 3,3-diphenyl-13-chloro-13-(2-oxo-2-ethoxyethyl)-1H-indeno[2,1-f]naphtho[1,2-b]pyran;
(c) 3,3-di(4-methoxyphenyl)-6,11-dimethyl-13-hydroxy-13-(2-oxo-2-ethoxyethyl)-1H-indeno[2,1-f]naphtho[1,2-b]pyran;
(d) 3-(4-methylphenyl)-3-(4-fluorophenyl)-13-chloro-13-(2-oxo-2-ethoxyethyl)-1H-indeno[2,1-f]naphtho[1,2-b]pyran;
(e) 3-(4-methoxyphenyl)-3-(2,3-dihydrobenzofur-5-yl)-6,11-difluoro-13-hydroxy-13-(2-oxo-2-ethoxyethyl)-1H-indeno[2,1-f]naphtho[1,2-b]pyran;
(f) 3-phenyl-3-(4-morpholinophenyl)-13-hydroxy-13-(1-oxo-2-methoxyprop-2-yl)-1H-indeno[2,1-f]naphtho[1,2-b]pyran; and
(g) 3-phenyl-3-(4-morpholinophenyl)-6,11-dimethyl-13-chloro-13-(1-carboxyethyl)-1H-indeno[2,1-f]naphtho[1,2-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance(s) is incorporated or applied.

9. The photochromic article of claim 8 wherein the article is a lens.

10. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

18. The photochromic article of claim 15 wherein the organic photochromic compound (b) is selected from the group consisting of naphthopyrans, benzopyrans, phenanthropyrans, spiro(benzindoline)naphthopyrans, spiro(indoline)benzopyrans, spiro(indoline)naphthopyrans, spiro(indoline)quinopyrans, spiro(indoline)pyrans, spiro(indoline)naphthoxazines, spiro(indoline)pyridobenzoxazines, spiro(benzindoline)pyridobenzoxazines, spiro(benzindoline)naphthoxazines, spiro(indoline)benzoxazines and mixtures of such photochromic compounds.

19. The photochromic article of claim 18 wherein the photochromic compound is present in an amount of from about 0.05 to 1.0 milligram per square centimeter of organic host material surface to which the photochromic substance(s) is incorporated or applied.

20. The photochromic article of claim 19 wherein the article is a lens.

21. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 2, and (b) at least one other organic photochromic compound having at least one activated absorption maxima within the range of between about 400 and 700 nanometers.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

23. A naphthopyran compound represented by the following graphic formula:

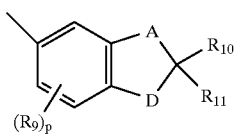

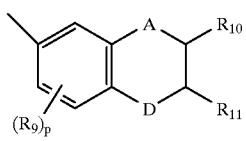

wherein, (a) $R_1$ is hydrogen, hydroxy or chloro and $R_2$ is the group, —CH(V)$_2$, wherein V is —CN or —COOR$_5$, and each $R_5$ is hydrogen, $C_1$–$C_6$ alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl or the unsubstituted, mono- or di-substituted aryl groups phenyl or naphthyl, or $R_2$ is the group, —CH($R_6$)Y, wherein $R_6$ is hydrogen, $C_1$–$C_6$ alkyl or the unsubstituted, mono- or di-substituted aryl groups phenyl or naphthyl, and Y is —COOR$_5$, —COR$_7$, or —CH$_2$OR$_8$, wherein $R_7$ is hydrogen, $C_1$–$C_6$ alkyl, the unsubstituted, mono- or di-substituted aryl groups phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, or piperidino; $R_8$ is hydrogen, —COR$_5$, $C_1$–$C_6$ alkyl, $C_1$–$C_3$ alkoxy ($C_1$–$C_6$)alkyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, or the unsubstituted, mono- or di-substituted aryl groups phenyl or naphthyl, each of all of said aryl group substituents being $C_1$–$C_6$ alkyl or $C_1$–$C_6$ alkoxy;

(b) $R_3$ and $R_4$ are each $C_1$–$C_6$ alkyl, $C_1$–$C_6$ alkoxy, chloro, or fluoro, and m and n are each the integers 0, 1, or 2;

(c) B and B' are each selected from the group consisting of:
(i) the unsubstituted, mono-, di-, and tri-substituted aryl groups, phenyl and naphthyl;

(ii) the unsubstituted, mono-, and di-substituted aromatic heterocyclic groups pyridyl, furanyl, benzofuran-2-yl, benzofuran-3-yl, thienyl, benzothien-2-yl and benzothien-3-yl, said aryl and aromatic heterocyclic substituents in (c)(i) and (ii) being selected from the group consisting of hydroxy, amino, mono($C_1$–$C_6$)alkylamino, di($C_1$–$C_6$) alkylamino, piperidino, morpholino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, chloro and fluoro;

(iii) the groups represented by the following graphic formulae:

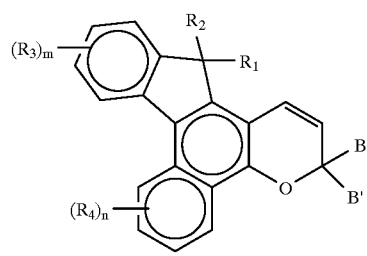

wherein A is carbon or oxygen and D is oxygen or substituted nitrogen, provided that when D is substituted nitrogen, A is carbon, said nitrogen substituents being selected from the group consisting of hydrogen, $C_1$–$C_6$ alkyl and $C_2$–$C_6$ acyl; each $R_9$ is $C_1$–$C_6$ alkyl, $C_1$–$C_6$ alkoxy, hydroxy, chloro or fluoro; $R_{10}$ and $R_{11}$ are each hydrogen or $C_1$–$C_6$ alkyl; and p is the integer 0, 1 or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)-cycloalkyl, chloro ($C_3$–$C_6$)cycloalkyl and fluoro($C_3$–$C_6$)cyclo-alkyl; and (v) the group represented by the following graphic formula:

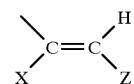

wherein X is hydrogen or $C_1$–$C_4$ alkyl and Z is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, fluoro or chloro; or (vi) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

24. The naphthopyran of claim 23 wherein,
(a) $R_1$ is hydrogen, hydroxy or chloro and $R_2$ is the group, —CH(V)$_2$, wherein V is —CN or —COOR$_5$, and each $R_5$ is hydrogen, $C_1$–$C_4$ alkyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl or the unsubstituted or mono-substituted aryl groups phenyl or naphthyl, or $R_2$ is the group, —CH($R_6$)Y, wherein $R_6$ is hydrogen, $C_1$–$C_4$ alkyl or the unsubstituted or mono-substituted aryl groups phenyl or naphthyl, and Y is —COOR$_5$, —COR$_7$, or —CH$_2$OR$_8$, wherein $R_7$ is hydrogen, $C_1$–$C_4$ alkyl, the unsubstituted or mono-substituted aryl groups phenyl or naphthyl, amino, mono($C_1$–$C_4$)alkylamino, di($C_1$–$C_4$)alkylamino, phenylamino, mono- or di-($C_1$–$C_4$)alkyl substituted phenylamino, mono- or di-($C_1$–$C_4$)alkoxy substituted phenylamino, diphenylamino, mono- or di-($C_1$–$C_4$)alkyl substituted diphenylamino, mono- or di-($C_1$–$C_4$)alkoxy substituted diphenylamino, morpholino or piperidino; $R_8$ is hydrogen, —COR$_5$, $C_1$–$C_4$ alkyl, $C_1$–$C_2$ alkoxy($C_1$–$C_4$)alkyl, phenyl($C_1$–$C_2$)alkyl, mono ($C_1$–$C_4$)alkyl substituted phenyl($C_1$–$C_2$)alkyl, mono ($C_1$–$C_4$)alkoxy substituted phenyl($C_1$–$C_2$)alkyl or the unsubstituted or mono-substituted aryl groups phenyl or naphthyl, each of all of said aryl group substituents being $C_1$–$C_4$ alkyl or $C_1$–$C_4$ alkoxy;

(b) $R_3$ and $R_4$ are each $C_1$–$C_4$ alkyl, $C_1$–$C_4$ alkoxy, chloro or fluoro, and m and n are each the integers 0 or 1;

(c) B and B' are each selected from the group consisting of:
 (i) phenyl, mono-substituted phenyl and di-substituted phenyl;
 (ii) the unsubstituted, mono-, and di-substituted aromatic heterocyclic groups furanyl, benzofuran-2-yl, thienyl and benzothien-2-yl, said phenyl and aromatic heterocyclic substituents in (c)(i) and (ii) being selected from the group consisting of hydroxy, amino, mono($C_1$–$C_3$)alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;
 (iii) the groups represented by the following graphic formulae:

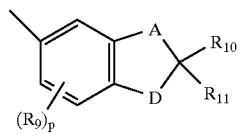

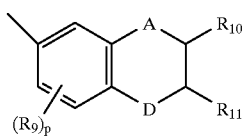

wherein A is carbon and D is oxygen, $R_9$ is $C_1$–$C_3$ alkyl or $C_1$–$C_3$ alkoxy, $R_{10}$ and $R_{11}$ are each hydrogen or $C_1$–$C_4$ alkyl; and p is the integer 0 or 1;
 (iv) $C_1$–$C_4$ alkyl; and (v) the group represented by the following graphic formula:

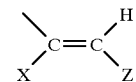

wherein X is hydrogen or methyl and Z is phenyl or mono-substituted phenyl, said phenyl substituent being selected from the group consisting of $C_1$–$C_3$ alkyl, $C_1$–$C_3$ alkoxy and fluoro; or
 (vi) B and B' taken together form a fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, each of said fluoren-9-xylidene substituents being selected from the group consisting of $C_1$–$C_3$ alkyl, $C_1$–$C_3$ alkoxy, fluoro and chloro.

25. The naphthopyran compound of claim 24 wherein, (a) $R_1$ is hydrogen, hydroxy or chloro and $R_2$ is the group, —CH(V)$_2$, wherein V is —CN, or $R_2$ is the group, —CH ($R_6$)Y, wherein $R_6$ is hydrogen or $C_1$–$C_4$ alkyl, and Y is —COOR$_5$ or —CH$_2$OR$_8$, wherein $R_5$ is hydrogen or $C_1$–$C_4$ alkyl, $R_8$ is hydrogen, —COR$_5$ or $C_1$–$C_4$ alkyl;

(b) $R_3$ and $R_4$ are each $C_1$–$C_3$ alkyl or $C_1$–$C_3$ alkoxy, and m and n are each the integers 0 or 1; and (c) B and B' are each selected from the group consisting of phenyl, mono-, and di-substituted phenyl, unsubstituted, mono-, and di-substituted aromatic heterocyclic groups furanyl, benzofuran-2-yl, thienyl and benzothien-2-yl, each of said phenyl and aromatic heterocyclic substituents being selected from the group consisting of hydroxy, $C_1$–$C_3$ alkyl, $C_1$–$C_3$ alkoxy, fluoro and chloro; and the group represented by the following graphic formula:

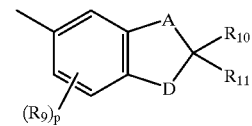

wherein A is carbon and D is oxygen, $R_9$ is $C_1$–$C_3$ alkyl or $C_1$–$C_3$ alkoxy, $R_{10}$ and $R_{11}$ are each hydrogen or $C_1$–$C_3$ alkyl, and p is the integer 0 or 1; or B and B' taken together form fluoren-9-ylidene, adamantylidene, bornylidene, norbornylidene or bicyclo(3.3.1)nonan-9-ylidene.

* * * * *

UNITED STATES PATENT AND TRADEMARK OFFICE
CERTIFICATE OF CORRECTION

PATENT NO. : 5,955,520
DATED : September 21, 1999
INVENTOR(S) : Harry G. Heller et al.

It is certified that error appears in the above-identified patent and that said Letters Patent is hereby corrected as shown below:

Column 25, claim 23,
Lines 19-33, "23. A naphthopyran compound represented by the following graphic formula:" should be followed by the following graphic formula.

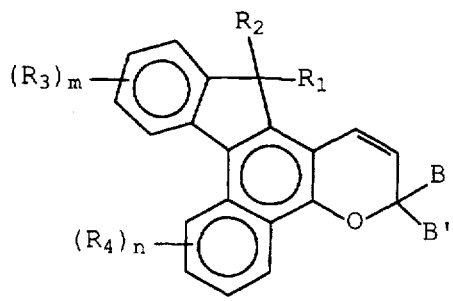

Column 26, claim 23 (c) (iii),
Lines 12-23, " (iii) the groups represented by the following graphic formulae:" should be followed by the following graphic formulae:

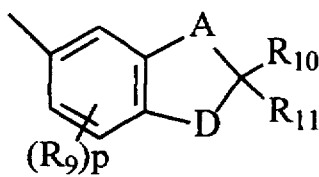 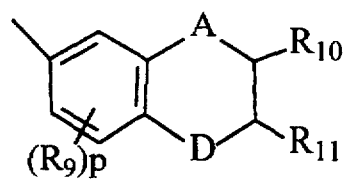

Signed and Sealed this

Twenty-fifth Day of December, 2001

Attest:

JAMES E. ROGAN
*Attesting Officer*   *Director of the United States Patent and Trademark Office*